(12) United States Patent
Kollgaard et al.

(10) Patent No.: US 7,574,915 B2
(45) Date of Patent: Aug. 18, 2009

(54) SIMPLIFIED IMPEDANCE PLANE BONDTESTING INSPECTION

(75) Inventors: Jeffrey R. Kollgaard, Kent, WA (US); Nancy L. Wood, Clayton, MO (US)

(73) Assignee: The Boeing Company, Chicago, IL (US)

( * ) Notice: Subject to any disclaimer, the term of this patent is extended or adjusted under 35 U.S.C. 154(b) by 306 days.

(21) Appl. No.: 11/617,304

(22) Filed: Dec. 28, 2006

(65) Prior Publication Data
US 2008/0156096 A1 Jul. 3, 2008

(51) Int. Cl.
*G01N 29/09* (2006.01)
(52) U.S. Cl. .......................................................... 73/582
(58) Field of Classification Search .................. None
See application file for complete search history.

(56) References Cited

U.S. PATENT DOCUMENTS

| | | | | |
|---|---|---|---|---|
| 3,016,735 | A | * | 1/1962 | Arnold et al. .................. 73/588 |
| 3,453,872 | A | | 7/1969 | Botsco |
| 3,564,903 | A | | 2/1971 | Woodmansee et al. |
| 4,215,583 | A | | 8/1980 | Botsco et al. |
| 4,815,001 | A | * | 3/1989 | Uthe et al. ................... 700/212 |
| 4,840,066 | A | | 6/1989 | Botsco et al. |
| 4,862,384 | A | * | 8/1989 | Bujard et al. .................. 702/54 |
| 6,298,726 | B1 | * | 10/2001 | Adachi et al. .................. 73/632 |
| 7,222,514 | B2 | * | 5/2007 | Kollgaard et al. .............. 73/1.82 |
| 2005/0279171 | A1 | | 12/2005 | Kollgaard et al. |
| 2007/0126422 | A1 | * | 6/2007 | Crouch et al. ............... 324/240 |

FOREIGN PATENT DOCUMENTS

GB 2425179 A 10/2006

OTHER PUBLICATIONS

Ultrasonic Testing Applications In Advanced Materials And Processes, *Nondestructive Testing Handbook*, p. 515, vol. 7, Nondestructive Testing Handbook, Second Edition.
International Search Report for PCT/US2007/023456 dated Jun. 11, 2008.

* cited by examiner

*Primary Examiner*—Hezron Williams
*Assistant Examiner*—Rose M Miller
(74) *Attorney, Agent, or Firm*—Alston & Bird LLP

(57) ABSTRACT

An NDI system includes an ultrasonic transducer and an electronic device having an indicator, such as a light source. The electronic device energizes the transducer, receives sinusoidal signals from the transducer, determines impedance-plane coordinates corresponding to quadrature-phase separated components of the sinusoidal signals, and automatically activates the indicator if impedance-plane coordinates exceed a preset threshold. The system may be used in methods of inspecting layered structures such as composite aircraft components and repair patches applied to such structures.

20 Claims, 6 Drawing Sheets

SIMPLIFIED IMPEDANCE PLANE BONDTESTING INSPECTION

FIELD OF THE INVENTION

Embodiments of the present invention relate generally to ultrasonic inspections of structures. More particularly, embodiments of the invention relate to systems and methods for non-destructive ultrasonic inspections of sub-surface portions of layered structures.

BACKGROUND OF THE INVENTION

Laminate composite materials are becoming increasingly common in the constructions of large aircraft. Typical laminate composite materials are composed of layered resin bonded graphite textiles. Like any material disposed along the exterior of an aircraft, laminate composite materials are subject to damages during the service life of an aircraft. In-flight collisions with birds and air-borne debris, and ground collisions involving loading and maintenance vehicles and equipment cause visible impact sites along the exterior of an aircraft. Assessments and repairs of laminate composite materials represent significant challenges with regard to efficiencies in time, cost, and training. Ground maintenance crews may be able to recognize impact sites along aircraft exteriors, but are typically not sufficiently trained or equipped to assess damages that may be associated with impact sites.

Damages within a composite aircraft component tend to initiate at impact sites and propagate into structures in expanding cone patterns. Unfortunately, visible impact sites that represent mere superficial markings are not easily distinguished by visual inspection from those overlying significant internal damages. Non-destructive inspection (NDI) devices are available so that inspections can reveal hidden sub-surface damages. However, typical available technologies require considerable training and experience.

For example, a bond-testing apparatus according to an example of prior art is disclosed in the U.S. Pat. No. 4,215,583 issued to Botsco et al. on Aug. 5, 1980, which patent is incorporated herein by this reference. This patent describes a sonic energy probe that receives a sinusoidal reference signal from an oscillator and develops an output signal that contains phase and amplitude data. The phase and amplitude data contained by the output signal developed by the probe are affected by properties of an inspected structure coupled to the probe. When the probe is disposed against a layered structure having a disbond, the phase difference between the reference signal and the output signal tends to increase with the depth of the disbond. The amplitude of the output signal tends to decrease with the depth of the disbond. Thus, when the amplitude and phase difference are related respectively to radius and angle in a two-dimensional polar coordinate display called a complex impedance plane display, typical data points fall along a spiral pattern. Shallow disbonds are represented in outer portions of the spiral pattern, and deeper disbonds are represented in inner portions of the spiral pattern, for example, as shown in FIG. 3 of the above-identified patent to Botsco et al. While the position of a data point in a complex impedance plane display may provide information about the condition of a structure under inspection, a high degree of training is needed for understanding and using the described apparatus. Thus, like other available NDI approaches, the technology described in the patent to Botsco et al. appears to be in the practice domain of highly trained specialists.

Despite the complexities of aircraft inspection technologies, many of the challenges faced in commercial aviation can be understood at a level where basic human safety, customer satisfaction, and economic feasibilities are the critical issues. A typical scenario faced by commercial airlines occurs when a ground maintenance crew member spots an impact site along the exterior of an aircraft as the craft is serviced between flights. A decision must be made as to whether the aircraft should be permitted to fly or should be grounded for thorough inspections, damage assessments, and repairs if necessary. Consequences can be severe when such a decision is poorly made. Both safety and commercial viability must be preserved. Thus an aircraft with significant subsurface damages along a wing or other structure should be grounded, and an aircraft having mere surface markings but no structural damages should be dispatched for flight. Trained NDI specialists and the complex equipment they may need to deploy are not typically immediately available at commercial aviation facilities. If specialists are to be summoned every time an impact site along the exterior of an aircraft is noticed, flight delays will occur, and passengers may need to be re-routed and possibly accommodated with hotel rooms and meals.

Thus, it would be advantageous to provide devices and methods for inspecting structures by modes requiring minimal training and interpretive expertise. Simplified methods in inspecting layered structures are needed. A need exists for rapid results providing go and no-go indications in NDI inspections.

BRIEF SUMMARY OF THE INVENTION

Embodiments of the invention may address at least some of the above needs and achieve other advantages. For example, a first aspect of the invention relates to a method of inspecting a structure. According to the method, an ultrasonic transducer is coupled with a first structure portion free of defects, and impedance-plane calibration coordinates corresponding to quadrature-phase separated components of a sinusoidal signal are determined. The ultrasonic transducer is lifted from the first structure portion, and impedance-plane lift-off coordinates corresponding to quadrature-phase separated components of a sinusoidal signal are determined. The ultrasonic transducer is coupled with a structure portion to be inspected and impedance-plane inspection coordinates corresponding to quadrature-phase separated components of a sinusoidal signal are determined. The calibration coordinates, lift-off coordinates, and inspection coordinates are rotated at least until the calibration coordinates and lift-off coordinates reach a first axis. An indicator is activated if the rotated inspection coordinates are at least disposed above the first axis. In at least one embodiment of the method, the indicator is activated if the rotated inspection coordinates are at least disposed above the first axis and spaced from the first axis by at least the preset threshold. Determination of the calibration and lift-off coordinates may be caused by the actuations of first and second switches, respectively.

A second aspect of the invention relates to a method of inspecting an airplane structure. According to the method, an ultrasonic transducer is coupled with a first structure portion free of defects and impedance-plane calibration coordinates are determined. The ultrasonic transducer is lifted from the first structure portion and impedance-plane lift-off coordinates are determined. The ultrasonic transducer is coupled with an airplane structure to be inspected and impedance-plane inspection coordinates are determined. Whether a defect is present in the airplane structure is automatically determined according to the calibration coordinates, lift-off coordinates, and inspection coordinates. In at least one embodiment of the method, an indicator is activated if a defect is determined to be present in the airplane structure. Automatically determining whether a defect is present in the airplane structure may entail automatically rotating the calibration coordinates, lift-off coordinates, and inspection coordinates. For example, the calibration coordinates, lift-off coordinates, and inspection coordinates may be automatically rotated at least until the calibration coordinates and lift-off coordinates reach a first axis. In that example, automatically determining whether a defect is present in the airplane structure may entail determining that a defect is present in the airplane structure if the rotated inspection coordinates are at least disposed above the first axis.

A third aspect of the invention relates to a system that includes an ultrasonic transducer and an electronic device having an indicator, which may be, for example, a light source. The electronic device is disposed in electrical contact with the ultrasonic transducer and is capable of energizing the transducer, receiving sinusoidal signals generated by the transducer, determining impedance-plane coordinates corresponding to quadrature-phase separated components of the signals generated by the transducer, determining whether at least one impedance-plane coordinate exceeds a preset threshold, and automatically activating the indicator if the at least one impedance-plane coordinate exceeds the preset threshold. The electronic device may include a first switch and a second switch, and may be adapted to determine first impedance plane coordinates upon actuation of the first switch and second impedance plane coordinates upon actuation of the second switch. The electronic device may further be configured to automatically rotate the first and second impedance plane coordinates. The electronic device may be further yet configured to automatically rotate the first and second impedance plane coordinates, for example, until the second impedance plane coordinates exceed the preset threshold.

BRIEF DESCRIPTION OF THE SEVERAL VIEWS OF THE DRAWINGS

Having thus described the invention in general terms, reference will now be made to the accompanying drawings, which are not necessarily drawn to scale, and which are briefly described below.

Figure 1:
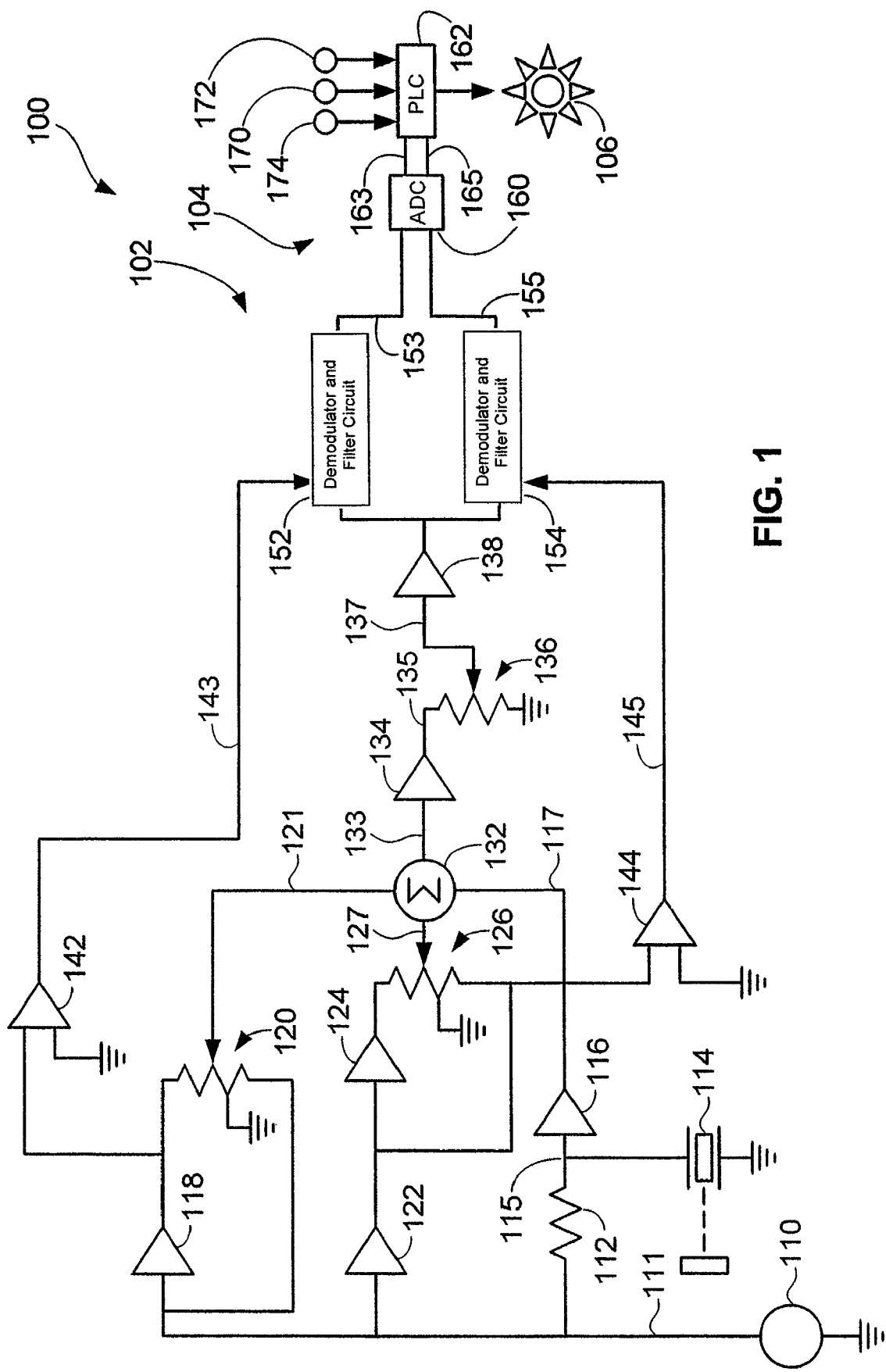

FIG. 1 illustrates an ultrasonic inspection system, in accordance with at least one embodiment of the present invention, having an ultrasonic transducer, an analog signal processing circuit portion, a digital processing circuit portion, and an indicator for alerting an operator when damages are detected.

Figure 2:
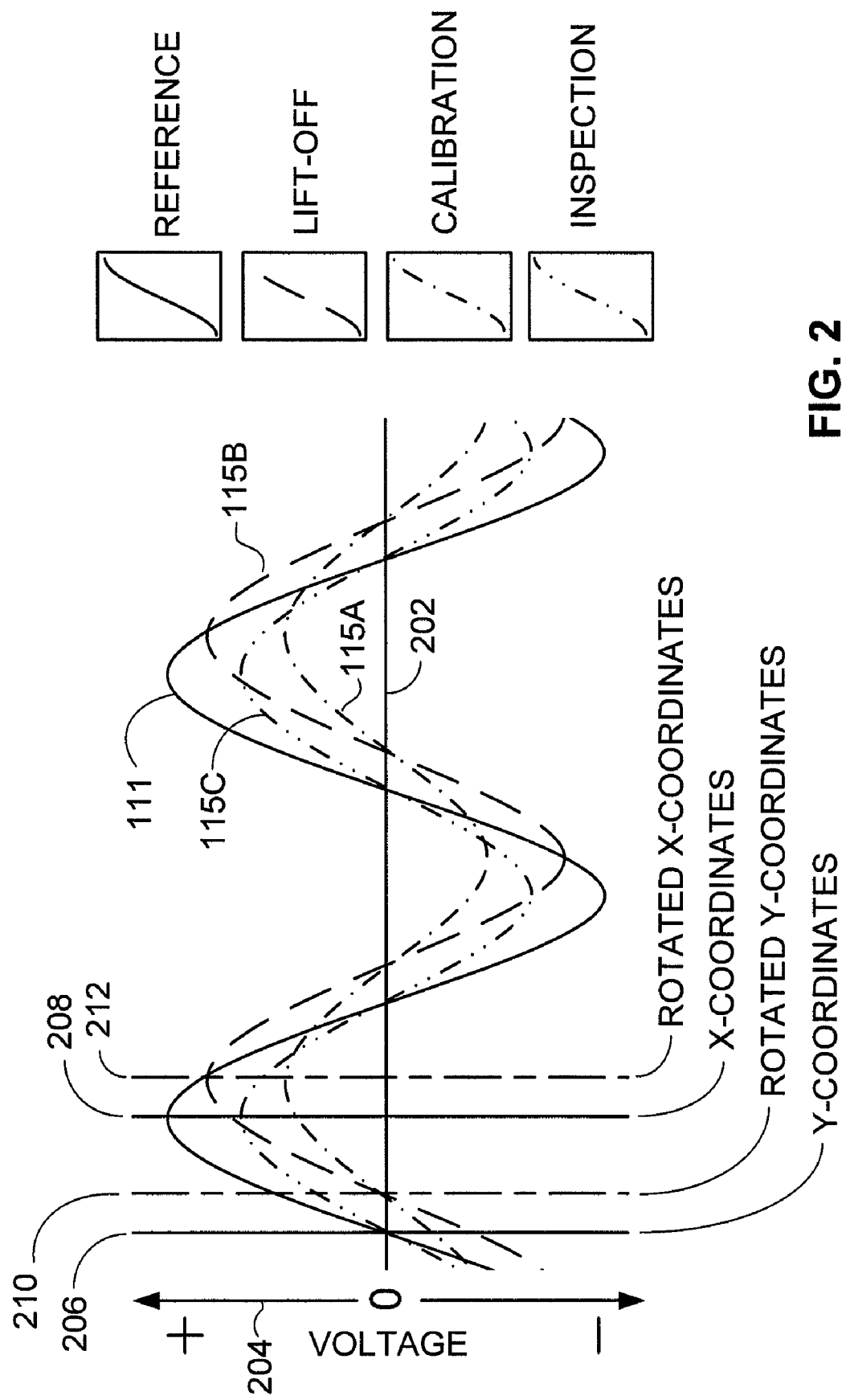

FIG. 2 is a graphical representation of response signals, developed under several different load conditions, by the transducer of the system of FIG. 1.

Figure 3:
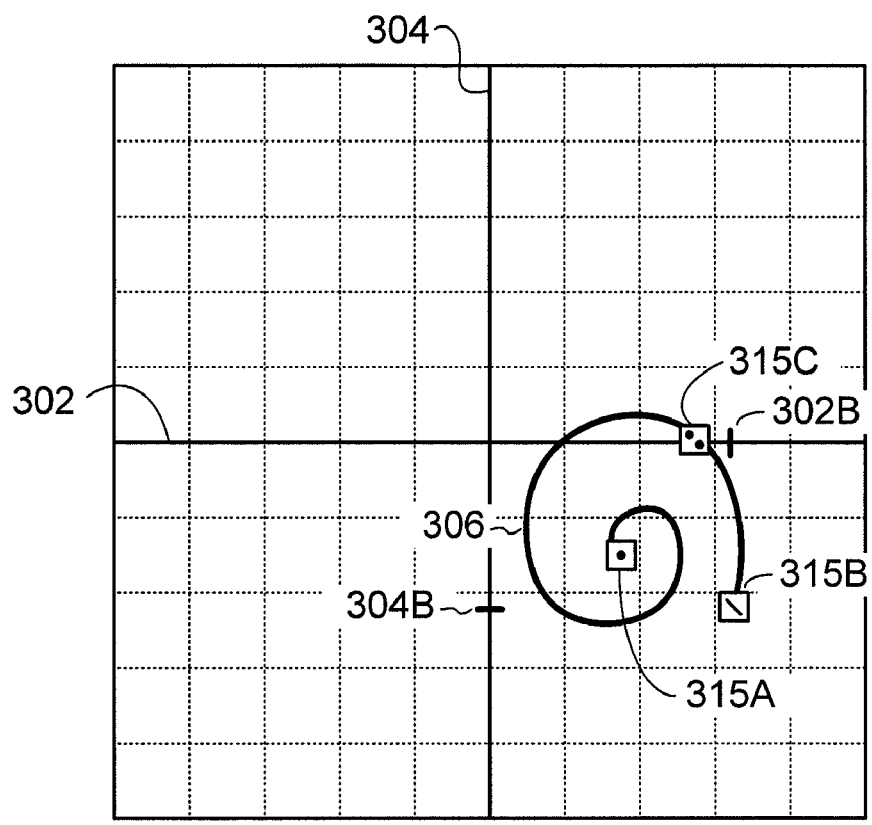

FIG. 3 is a graphical representation of an impedance plane wherein the response signals of FIG. 2 are represented as coordinates.

Figure 4:
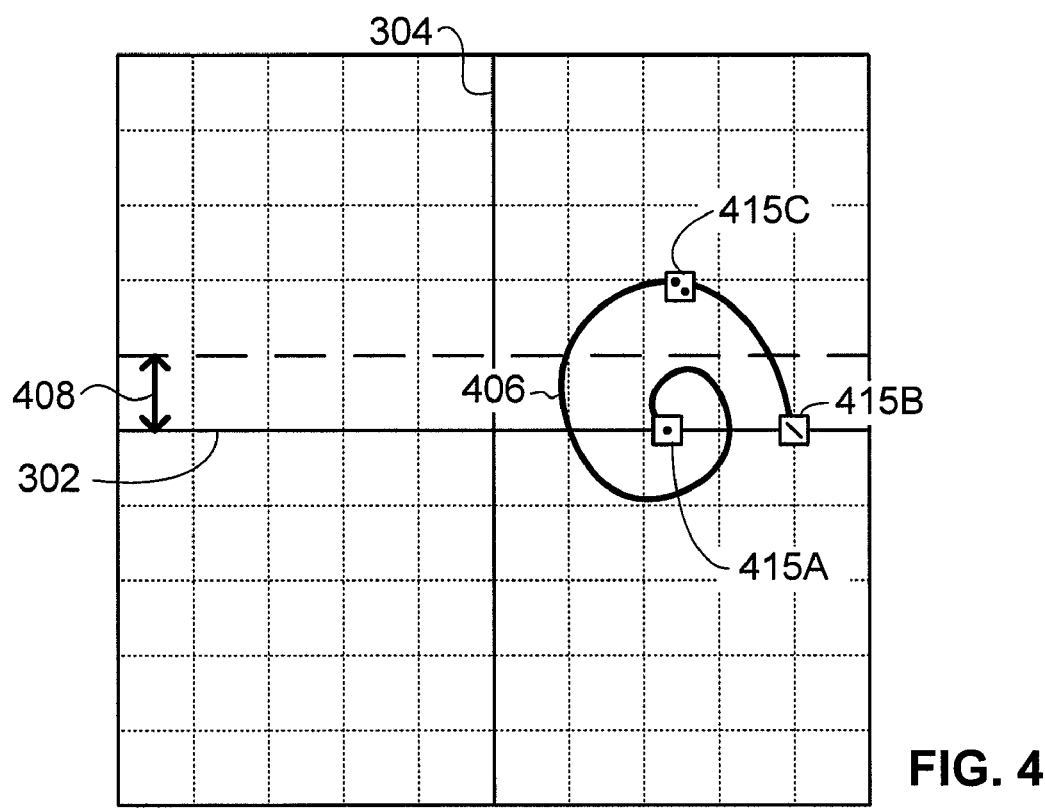

FIG. 4 is a graphical representation of an impedance plane wherein the impedance plane coordinates of FIG. 3 are rotated and an alert threshold is defined.

Figure 5:
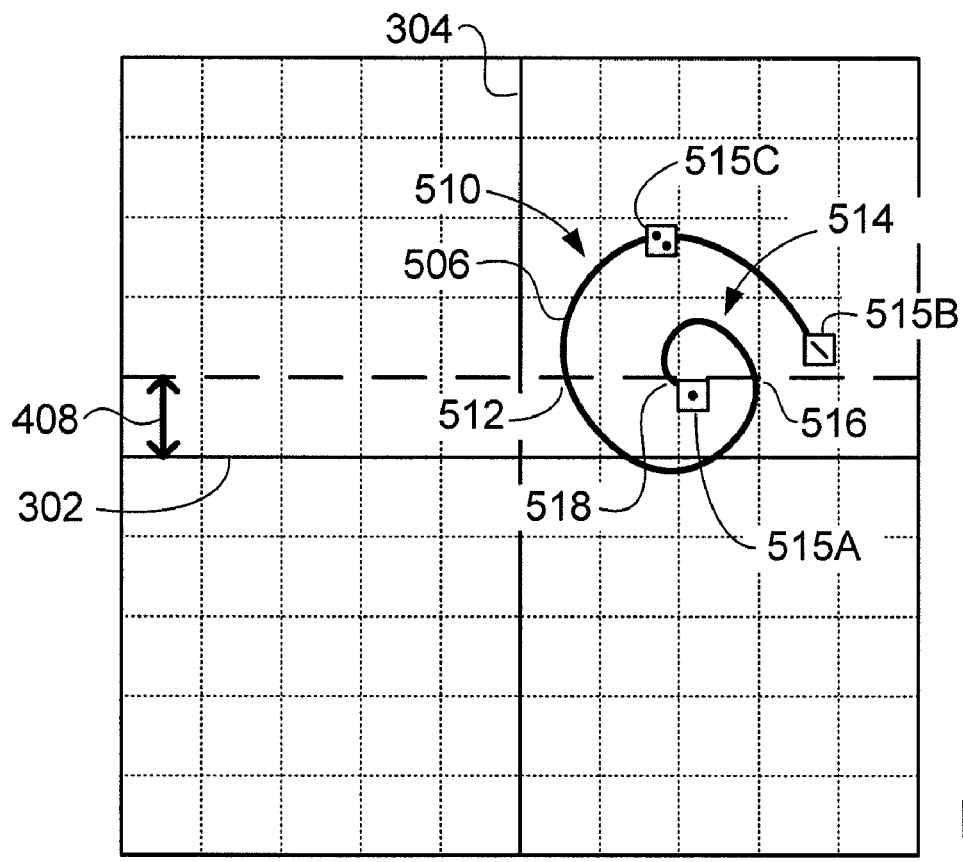

FIG. 5 is a graphical representation of an impedance plane wherein the impedance plane coordinates of FIG. 3 are rotated such that a lift-off condition during an inspection session corresponds to coordinates that are disposed above the threshold defined in FIG. 4.

Figure 6:
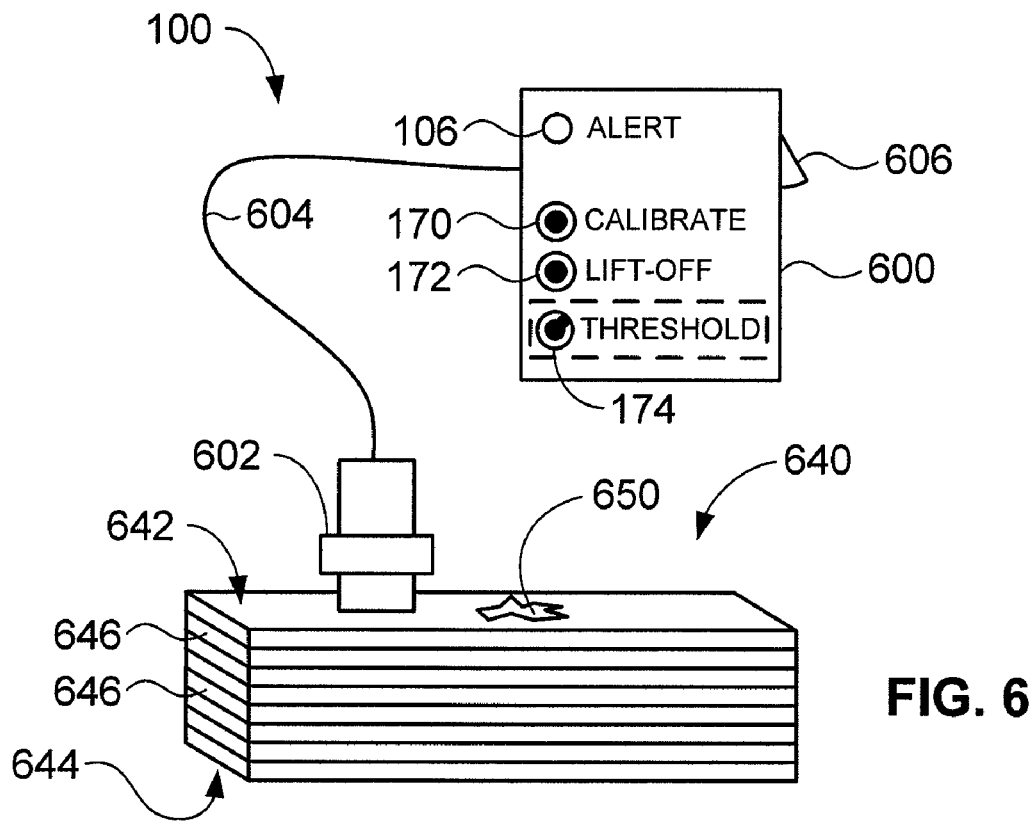

FIG. 6 is a diagrammatic environmental view of the inspection system of FIG. 1 shown inspecting a structure free of sub-surface flaws as revealed by the inactivity of the indicator.

Figure 7:
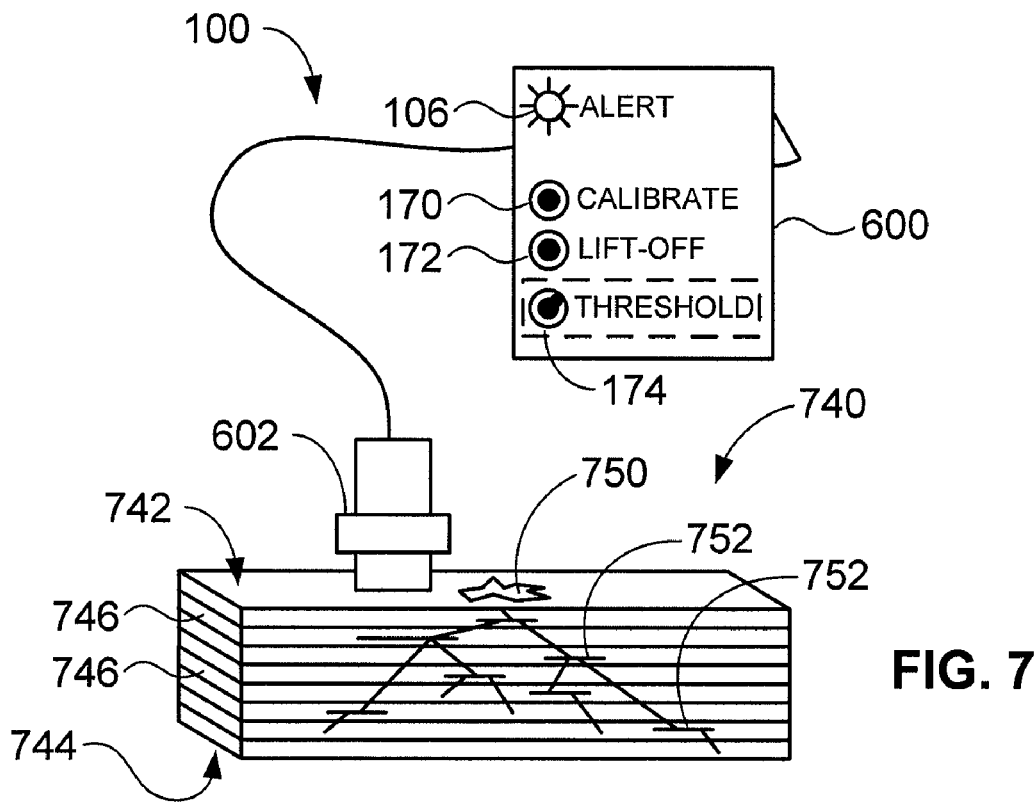

FIG. 7 is a diagrammatic environmental view of the inspection system of FIG. 1 shown inspecting a structure having sub-surface flaws as revealed by the activation of the indicator.

Figure 8:
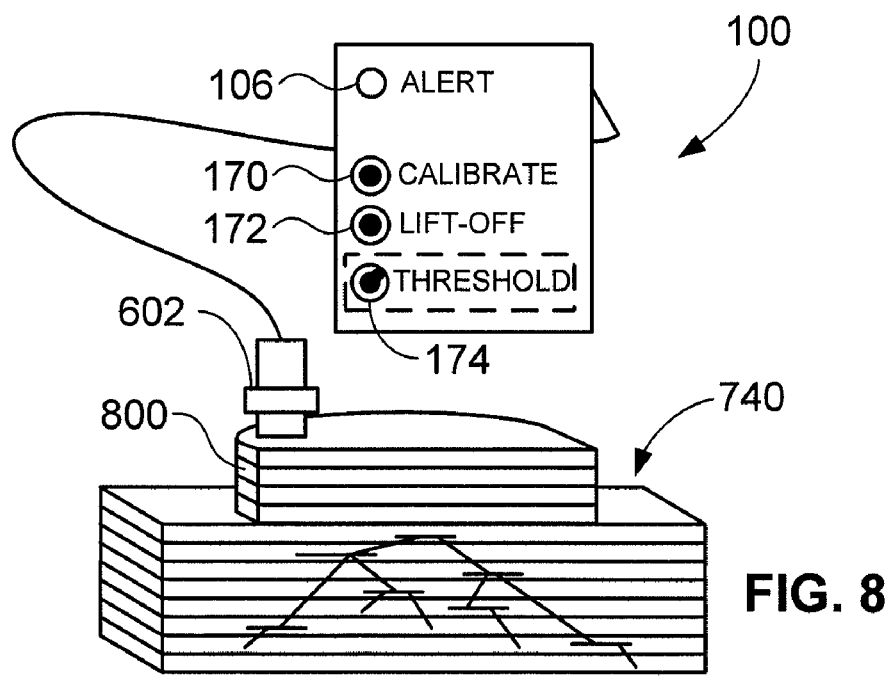

FIG. 8 is a diagrammatic environmental view of the inspection system of FIG. 1 shown inspecting the bondline integrity of a repair patch applied to the damaged structure of FIG. 7.

Figure 9:
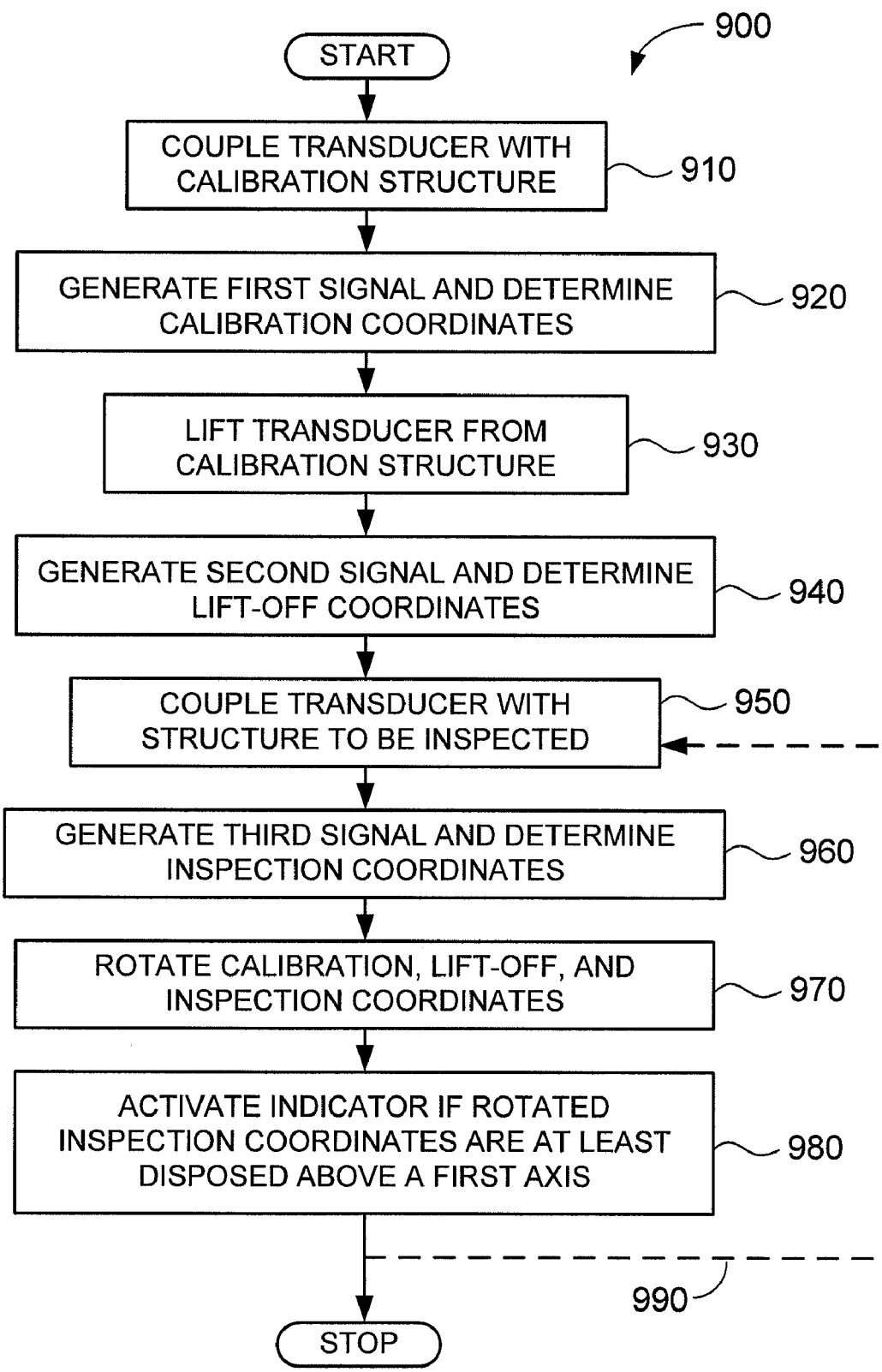

FIG. 9 is a block diagram representing a method of inspecting a structure, the method in accordance with at least one other embodiment of the present invention.

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

An inspection system 100 according to at least one embodiment of the invention is shown in FIG. 1. The inspection system includes an analog signal-processing portion 102 and a digital processing portion 104. With regard to the analog signal-processing portion 102 of the inspection system 100, an oscillator 110 produces a sinusoidal reference signal 111 that is applied to a combination of a resistor 112 and an ultrasonic transducer 114. When the ultrasonic transducer 114 is placed in contact or coupling with a layered structure under inspection, the complex impedance of the transducer 114 is affected by the physical characteristics of the structure. Thus, the response signal 115 developed by the transducer 114 has phase and amplitude characteristics that are generally representative of the structure under inspection, and that are more particularly representative of the locations of defects such as bond flaws between the various layers of the structure. The response signal 115 is applied to a buffer amplifier 116, which produces the signal 117 that has phase and amplitude characteristics derived from those of response signal 115.

The sinusoidal signal 111 is further applied to an inverting amplifier 118, which, in conjunction with a potentiometer 120, produces a signal 121. The reference signal 111 is also applied to an integrating amplifier 122, which, in conjunction with an inverting amplifier 124 and potentiometer 126, produces a signal 127. Signal 121 and signal 127 represent quadrature-phase separated components of the response signal 115 developed by the transducer 114.

The signals 121, 127, and 117 are applied to a summing junction 132 to produce a signal 133, which represents the complex impedance of the transducer 114 as affected by any flaws present in the bonding between layers of a laminate structure under inspection. The signal 133 is applied to a buffer amplifier 134, the output signal 135 of which is applied to one terminal of a potentiometer 136. A signal 137, which is an attenuated form of the signal 133, then reaches an amplifier 138, the output of which is applied to a pair of synchronous demodulator and filter circuits 152 and 154. In order for the circuits 152 and 154 to develop components of the signal 133, reference signals 143 and 145 are provided respectively by voltage comparators 142 and 144.

The 152 and 154 circuits respectively provide the first and second component signals 153 and 155. The first component signal 153 may be mathematically described as Ep(cos(phi)), and the second component signal 155 as Ep(sin(phi)), where phi represents the phase characteristic of the signal 133. Thus, the first and second component signals 153 and 155 have amplitudes that are proportional to quadrature-phase separated components of the signal 133 which, when the transducer 114 is placed in contact or coupling with a structure under inspection, represents the condition of the structure.

Analog signal-processing in complex impedance plane analysis circuits is described in further detail in the U.S. Pat. No. 4,215,583, which issued to Botsco et al. on Aug. 5, 2003, and which is hereby incorporated herein in its entirety by this reference. In the Botsco patent, quadrature-phase separated components of a sinusoidal signal are used as coordinates in two-dimensional displays that represent vector tips in a complex impedance plane and that convey information relating to the amplitudes and phases of signals influenced by bond flaws within an inspected structure. It is therefore well understood in the prior art that the first and second component signals 153 and 155 can be related to impedance plane coordinates. Thus, the impedance plane coordinates described herein are determined by sampling the first and second component signals 153 and 155 respectively at the 152 and 154 circuits.

With regard to the present invention, according to the embodiment thereof represented in FIG. 1, the digital processing portion 104 of the system 100 receives the first and second component signals 153 and 155, and, as described in the following, an indicator 106 alerts an operator to the presence of a bond flaw when the transducer 114 is disposed into contact or coupling with a damaged or delaminated layered structure without regard to whether a typical operator views a two-dimensional display. This represents a significant advantage provided by embodiments of the present invention with regard to reducing the training and experience required of operators conducting inspections of laminated structures. Nonetheless, the first and second component signals 153 and 155, and other signals generated by or coursing through the system 100, may be available at test points within the circuit for sampling, analysis, and display by trained specialists.

The digital processing portion 104 comprises an analog-to-digital converter (ADC) 160, which receives the first and second component signals 153 and 155 and generates respectively corresponding digital data signals 163 and 165. The digital data signals 163 and 165 are communicated to a programmable logic chip (PLC) 162. The PLC 162 is programmed to activate an indicator 106, which can be, for example, a light-emitting diode (LED) or other light source, when evidence of the presence of a disbond or other flaw is detected. The conditions under which the PLC 162 activates the indicator 106 are described in the following.

In FIG. 2, an example of a reference signal 111 produced by the oscillator 110 (FIG. 1) is shown. The first axis 202 represents time and the vertical axis 204 represents time-varying voltage values. While FIG. 2 relates generally to other time and voltage domains, in this example the reference signal 111 has a maximum amplitude of several volts and a frequency of approximately 239 kilo-Hertz. The reference signal 111 is shown with several curves representing the response signals 115 developed by the transducer 114 under several different load conditions. It should be understood that FIGS. 2-5 depict simulated signals and coordinates determined therefrom.

In FIG. 2, a first response signal 115A corresponds to a calibration condition and is exhibited when the activated transducer 114 (FIG. 1) is disposed into contact or coupling with a good structure that is free of disbonds and flaws in the vicinity of the transducer. A second response signal 115B corresponds to a lift-off condition and is exhibited, upon activation by the oscillator 110, when the transducer 114 is out of coupling with a surface to be inspected. A third response signal 115C corresponds to an inspection condition and is exhibited when the activated transducer 114 is disposed into contact or coupling with a structure under inspection. The third response signal 115C has phase and amplitude characteristics that differ from those of the first response signal 115A. Thus, the third response signal 115C provides evidence that the structure under inspection may have a disbond or other defect in the vicinity of the transducer.

In FIG. 3, the signals depicted in FIG. 2 are represented as coordinates disposed within a two-dimensional complex impedance plane 300 defined by a first axis 302 and a second axis 304, which is perpendicular to the first axis 302. The impedance plane coordinates 315A, 315B, and 315C in FIG. 3 correspond respectively to the first, second, and third response signals 115A, 115B, and 115C in FIG. 2. Each of the impedance plane coordinates 315A, 315B, and 315C in FIG. 3 are defined by a first axis coordinate and a second axis coordinate, values of which are determined as shown in FIG. 2. Each second axis coordinate in FIG. 3 represents a measured voltage value for the respectively corresponding response signal at the time 206 of the zero voltage crossing of the reference signal 111 in FIG. 2. That is, for example, the second axis coordinate 304B of the impedance plane coordinates 315B in FIG. 3 represents the value of the response signal 115B in FIG. 2 at the time 206. Each first axis coordinate in FIG. 3 represents a measured voltage value for the respectively corresponding response signal at the time 208 in FIG. 2. That is, for example, the first axis coordinate 302B of the impedance plane coordinates 315B in FIG. 3 represents the value of the response signal 115B in FIG. 2 at the time 208.

The time 208 (FIG. 2) is spaced from the time 206 along the time axis 202 by one quarter of the oscillatory period of the sinusoidal reference signal 111. Thus, in terms of the angular phase of the sinusoidal reference signal 111, the time 208 can be described as disposed ninety degrees from the zero-voltage crossing, at time 206, of the reference signal 111. Furthermore, the first axis and second axis coordinates in FIG. 3 can be described as quadrature-phase separated components of the response signals to which the impedance plane coordinates respectively correspond. It should be understood that, while they are graphically illustrated together in FIG. 2, the response signals 115A, 115B, and 115C, are not generated simultaneously as they represent varying physical dispositions of the transducer 114 (FIG. 1). It should be further understood that the times 206 and 208 are defined in relation to the periodic zero-voltage crossing times of the sinusoidal reference signal 111, such that the times 206 and 208 are repeated with each sinusoidal cycle of the reference signal.

As the impedance plane coordinates 315A in FIG. 3 correspond to the first response signal 115A (FIG. 2) of the calibration condition with the activated transducer disposed into contact or coupling with a good structure, the coordinates 315A are identified herein as examples of impedance-plane calibration coordinates 315A. Similarly, the coordinates 315B in FIG. 3 are identified herein as impedance plane lift-off coordinates 315B, and the coordinates 315C are identified as impedance plane inspection coordinates 315C.

The PLC 162 in FIG. 1 receives the digital data signals 163 and 165, and is prompted to record these signals when a user actuates first and second switches 170 and 172. By actuation of the first switch 170, the user intends the condition of the transducer 114 to serve as the calibration condition. Thus, upon actuation of the first switch 170, the PLC 162 records the digital data signals 163 and 165 as impedance plane calibration coordinates along the first axis 302 and second axis 304, respectively, in FIG. 3. By actuation of the second switch 172, the user intends the condition of the transducer to serve as the lift-off condition. Thus, upon actuation of the second switch 172, the PLC 162 records the digital data signals 163 and 165 as impedance plane lift-off coordinates along the first axis 302 and second axis 304, respectively.

Once the impedance plane calibration coordinates and lift-off coordinates are established, the PLC 162 (FIG. 1) treats incoming digital data signals 163 and 165 as impedance plane inspection coordinates. The disposition of the inspection coordinates may vary in time as the user moves the transducer 114 into various positions along a structure under inspection and may encounter varying structure conditions such as defects. Thus the impedance plane inspection coordinates 315C in FIG. 3 may vary in real-time. As the third response signal 115C in FIG. 2 has phase and amplitude characteristics that differ from those of the first response signal 115A, the inspection coordinates 315C in this example do not coincide with the calibration coordinates 315A. Thus, the inspection coordinates 315C provide evidence that the structure under inspection may have a disbond or other defect in the vicinity of the transducer.

Generally, when the transducer 114 is disposed into contact or coupling with a structure in the vicinity of a defect such as a disbond between layers of the structure, the determined impedance-plane inspection coordinates will typically fall along a spiral path. For example, a simulated spiral path 306 is shown in FIG. 3. The spiral path 306 spirals inward from the lift-off coordinates 315B, which correspond to zero depth, to the calibration coordinates 315A, which correspond to the depth of a good undamaged structure. Typical inspection coordinates corresponding to disbonded or damaged portions of an inspected structure will typically fall somewhere along the spiral path 306 such that the position of the inspection coordinates along the path reveals the depth of a detected disbonded or damaged layer of the structure. Relatively shallow disbonds will typically be represented by inspection coordinates along the spiral path 306 toward the lift-off coordinates 315B. Relatively deep disbonds will typically be represented by inspection coordinates toward the calibration coordinates 315A. In FIG. 3, the inspection coordinates 315C fall along an outer portion of the spiral path 306, and toward the lift-off coordinates 315B. This provides evidence that the structure under inspection may have a shallow disbond or other defect in the vicinity of the transducer.

The PLC 162 (FIG. 1) generally rotates the impedance plane coordinates represented in FIG. 3. Such rotations produce rotated impedance plane coordinates as shown in FIGS. 4 and 5, which represent examples of embodiments of the present invention with regard to conditions under which the PLC 162 activates the indicator 106 (FIG. 1). In the example of FIG. 4, the PLC 162 automatically rotates the impedance plane coordinates 315A, 315B, and 315C until the resulting rotated calibration coordinates 415A and lift-off coordinates 415B reach the first axis 302. As shown in FIG. 4, such a rotation produces rotated inspection coordinates 415C and the rotated spiral path 406. Points along the rotated spiral path 406 in FIG. 4 relate in one-to-one correspondence with points along the spiral path 306 in FIG. 3.

Rotating impedance plane coordinates may be described as equivalent to shifting the times at which the voltage values of response signals are measured in determining the coordinates. That is, each of the rotated impedance plane coordinates in FIG. 4 has a second axis coordinate representing a voltage value measured at the time 210 in FIG. 2, and a first axis coordinate representing a measurement at the time 212. The respective correspondence of the calibration coordinates 415A (FIG. 4), lift-off coordinates 415B, and inspection coordinates 415C with the response signals 115A (FIG. 2), 115B, and 115C is maintained throughout the rotation. The shifted times 210 and 212 at which the response signals are measured in determining the rotated coordinates lag the times 206 and 208 respectively by a common time shift that is equivalent to the angular rotation represented by FIG. 4. Thus, like the times 206 and 208, the times 210 and 212 in FIG. 2 are separated by one quarter of the oscillatory period of the sinusoidal reference signal 111. Therefore, the rotated first axis and second axis coordinates in FIG. 4 can be described as quadrature-phase separated components of the response signals to which the rotated impedance plane coordinates respectively correspond.

In the example of FIG. 4, the PLC 162 (FIG. 1) activates the indicator 106 if the rotated inspection coordinates 415C are at least disposed above the first axis 302. This generally indicates an alarm condition wherein the rotated inspection coordinates, such as inspection coordinates 415C, are not coincident with the rotated calibration coordinates 415A. Furthermore, in the example of FIG. 4, the PLC 162 (FIG. 1) may be configured to activate the indicator 106 if the rotated inspection coordinates 415C are at least disposed above the first axis 302, and spaced from the first axis by at least a preset threshold 408. As shown in FIG. 1, the inspection system 100 comprises an adjustment device 174, such as a turn-potentiometer, for adjustment of the preset threshold 408, which may be adjusted to avoid spurious alarm indications when, for example, rotated inspection coordinates fall negligibly above the rotated calibration coordinates 415A.

In the example of FIG. 5, the PLC 162 (FIG. 1) automatically rotates the impedance plane coordinates 315A, 315B, and 315C (FIG. 3) until the resulting rotated lift-off coordinates 515B (FIG. 5) are disposed above the first axis 302 and spaced from the first axis by at least the preset threshold 408. As shown in FIG. 5, such a rotation produces rotated calibration coordinates 515A, rotated inspection coordinates 515C, and the rotated spiral path 506. In the example of FIG. 5, the PLC 162 (FIG. 1) activates the indicator 106 if the rotated inspection coordinates 515C are at least disposed above the first axis 302 and spaced from the first axis by at least the preset threshold 408. In this example, the indicator 106 (FIG. 1) is activated to alert an operator if coupling between the transducer 114 and an inspected structure is lost. Such a loss of coupling may cause the generation of rotated impedance plane coordinates near or at coincidence with the rotated lift-off coordinates 515B. Thus, in the example of FIG. 5, an operator is alerted when inadvertent lift-off and coupling-loss conditions occur.

Thus, with further regard to FIG. 5, the disposition of rotated inspection coordinates above the preset threshold 408 causes activation of the indicator 106 (FIG. 1). This establishes one or more depth ranges within which the inspection system 100 indicates disbonds within an inspected structure. For example, a first depth range is established along a first portion 510 of the rotated spiral path 506 between the rotated lift-off coordinates 515B and a first point 512 defined where the rotated spiral path 506 reaches the preset threshold 408. A second depth range is established above the threshold 408 and along a second portion 514 of the rotated spiral path 506 between second and third points 516 and 518, at which points the rotated spiral path 506 reaches the preset threshold 408. The first portion 510 represents an outer portion of the rotated spiral path 506, and the second portion 514 represents an inner portion of the rotated spiral path 506. Thus, the first portion 510 represents a shallow depth range for detected disbonds and the second portion 514 represents a deeper depth range. Nonetheless, in this example, rotated inspection coordinates falling along either the first portion 510 or the second portion 514 of the rotated spiral path 506 cause activation of the indicator 106 (FIG. 1) to alert an operator to the likely presence of a disbond in an inspected structure.

An embodiment of the inspection system 100 (FIG. 1) is shown in various simulated inspection scenarios in FIGS. 6-8. In this embodiment, many components of the inspection system 100 are disposed within and protected by a portable housing 600. A probe device 602 that includes the ultrasonic transducer 114 (FIG. 1) is connected to the remainder of the system 100 by a cable 604 so that the probe device can be moved about and coupled to structures while the housing 600 is held within view of an operator. The first and second switches 170 and 172 are readily available for actuation by an operator intending to establish calibration and lift-off coordinates. In the embodiment of the inspection device 100 shown in FIGS. 6-8, the adjustment device 174, which establishes the preset threshold 408 (FIG. 4), is intended for use by qualified NDI specialists and is therefore hidden within the housing 600. The indicator 106 is visible along the exterior of the housing so that an operator is made readily aware when an alert condition occurs. A power switch 606, when actuated, activates the inspection system 100 for use.

Prior to determining whether damages are present in a structure, the inspection device is calibrated by disposing the probe device 602 (FIG. 6) against a good structure that is free of disbonds and flaws in the vicinity of the probe device, and the first switch 170 is actuated. This establishes calibration coordinates, such as the calibration coordinates 315A in FIG. 3. The operator may choose a portion of a structure under inspection, under the assumption that the portion is free of flaws. However, the assurance of the calibration of the inspection system 100 following such a calibration procedure may be as questionable as any assumption that a good portion of a structure was interrogated. Thus, a calibration structure can be provided in order to assure that calibration is completed on a well characterized material sample. The operator furthermore lifts the probe device 602 from contact with any structure and actuates the second switch 172 to establish lift-off coordinates, such as the lift-off coordinates 315B in FIG. 3. The embodiment of the inspection system 100 shown in FIGS. 6-8 is configured as described herein with regard to FIG. 5. Thus, once the impedance plane calibration coordinates and lift-off coordinates are established, the inspection system is ready for use in inspecting structures. The indicator 106 will be activated to alert an operator if rotated inspection coordinates, for example coordinates 515C (FIG. 5), are disposed above the first axis 302 and spaced from the first axis by at least the preset threshold 408.

FIG. 6 depicts an exemplary laminate structure 640 capable of being used on any number of structures, such as those found on airplanes, automobiles and other vehicles, or any other structure that can benefit from a light, yet strong material. The laminate structure 640 has a front-surface 642 and a back-surface 644, and is composed of multiple individual laminate sheets 646. The laminate sheets are joined together by a bonding material. The exemplary laminate sheets 646 are composed of sheets of graphite fibers joined by a bonding material composed of an ester based resin. However, it should be appreciated that these descriptions relate to sheets constructed of other materials. Such other materials include, but are not limited to: carbon-based fabrics; metal foils; and polymer-based fabrics such as Kevlar®. Furthermore, while the laminate structure 640 of FIG. 6 is formed using an ester-based resin, these descriptions relate as well to other bonding materials.

In the course of normal use, laminate materials are subject to accidental damages. For example, where laminate materials are used to cover the front surfaces of aircraft wings, impact damages from birds and airborne debris can occur with every flight. In some instances the resultant damage will be very light, while in other instances the damage may be moderate to severe. For example, the laminate structure 640 in FIG. 6 is depicted as being so lightly damaged that a marking visibly apparent at an impact site 650 is merely superficial and represents no threat to the integrity of the structure. Thus, in the inspection scenario of FIG. 6, the indicator 106 is not activated to alert the operator that any damages are detected below the probe device 602. The rotated inspection coordinates in this scenario are coincident with the rotated calibration coordinates 515A (FIG. 5), are disposed below the threshold 408, and are indicative of a structure free of damages.

In FIG. 7, the inspection system 100 inspects a laminate structure 740 wherein flaws such as delaminations reside. In this figure, the impact site 750 is disposed above a damaged region of the structure. The damage likely began at the impact site along the front surface 742 of the structure and propagated toward the back surface 744 in an expanding cone pattern of disbonds 752 as illustrated. Such cone patterns are typical in damaged laminate structures as damages can extend both deeply into a structure and laterally around an impact site. Thus, when an impact site is observed on a surface, it is good practice to inspect a structure for hidden damages residing below surface portions that surround the impact site. Thus, in FIGS. 6 and 7, the probe device 602 is pressed against structures near the impact sites 650 and 750, respectively. In the scenario in FIG. 6, with an understanding that hidden damages typically exhibit cone patterns, the operator can determine that hidden damages are not likely present. In the scenario of FIG. 7, the rotated inspection coordinates 515C (FIG. 5) are disposed above the first axis 302 and spaced from the first axis by at least the preset threshold 408. Thus, the indicator 106 is activated to alert the operator that sub-surface damages are detected.

In FIG. 8, the inspection system 100 inspects the bondline integrity of a composite repair patch 800 applied to the damaged structure 740 of FIG. 7. Bondline integrity relates to the quality of the bond between a patch and the surface of a structure. If the bond has porosity or voids, the patch may become detached when the structure is returned to service. For example, a repair patch applied to the wing tip or other exterior component of a jet aircraft can be exposed to extreme conditions and can become detached and lost if the bondline integrity of the patch is not sound. Typical composite repair patches in the airline industry are either four or eight plies thick. In FIG. 8, the inspection system 100 has been initialized for inspecting the bondline integrity of a four-ply patch 800. That is, impedance plane calibration coordinates, collected using a calibration shim representing the thickness of the four-ply patch, and lift-off coordinates have been established. The indicator 106 is not activated in FIG. 8. This condition provides assurance to the operator that the repair patch 800 is properly applied to the damaged structure at least in the vicinity of the current position of the probe device 602. In performing a thorough inspection, the operator may move the probe device along the perimeter of the patch to determine whether the patch is well attached to the structure 740.

FIG. 9 is a flow chart representing a method, according to at least one embodiment of the invention, of inspecting a structure. The inspected structure may be, for example, an aircraft component constructed of multiple layers of composite material. The method 900 represented in FIG. 9 initiates at step 910, at which step an ultrasonic transducer is coupled with a first structure portion. The first structure portion is assumed or confirmed to be free of defects, and may be, for example, a calibration sample of material intended for use in calibrating the inspection system 100 (FIG. 7).

In step 920 (FIG. 9), a sinusoidal first signal is generated by the ultrasonic transducer and impedance plane calibration coordinates are determined, the calibration coordinates corresponding to quadrature-phase separated components of the first signal. For example, in step 920, the first response signal 115A in FIG. 2 may be generated as the sinusoidal first signal, and the impedance-plane calibration coordinates 315A in FIG. 3 may be determined.

In step 930 (FIG. 9), the ultrasonic transducer is lifted from the first structure portion. In step 940, a sinusoidal second signal is generated by the ultrasonic transducer and impedance plane lift-off coordinates are determined, the lift-off coordinates corresponding to quadrature-phase separated components of the second signal. For example, in step 940, the second response signal 115B in FIG. 2 may be generated as the sinusoidal second signal, and the impedance-plane lift-off coordinates 315B in FIG. 3 may be determined.

Once the impedance plane calibration coordinates and lift-off coordinates are established, the inspection of a structure, such as an aircraft component constructed of multiple layers of composite material, commences in step 950 (FIG. 9). In step 950, the ultrasonic transducer is coupled with a structure portion to be inspected. For example, an aircraft may be subject to a pre-flight visual inspection and the impact site 750 (FIG. 7), which represents a surface marking, dent, or scratch may come to the attention of a pre-flight inspector. The inspector may not be able to visibly determine whether serious damage is present, and a decision should be made as to whether the aircraft is fit for flying service. Accordingly, in this example, the inspector couples the probe device 602, which includes the ultrasonic transducer 114 (FIG. 1), with the structure 740 under inspection near the impact site as shown in FIG. 7.

In step 960 (FIG. 9), a sinusoidal third signal is generated by the ultrasonic transducer and impedance plane inspection coordinates are determined, the inspection coordinates corresponding to quadrature-phase separated components of the third signal. For example, in step 960, the third response signal 115C in FIG. 2 may be generated as the sinusoidal third signal, and the impedance-plane inspection coordinates 315C in FIG. 3 may be determined.

Rotations of the calibration coordinates, lift-off coordinates, and inspection coordinates are represented in FIG. 9 to occur in step 970. It should be understood this represents that the coordinates are rotated without regard to whether this is accomplished simultaneously. For example, the calibration and lift-off coordinates may be rotated prior to the determination of the inspection coordinates in step 960. In any event, the calibration coordinates, lift-off coordinates, and inspection coordinates are rotated in the method 900 at least until the calibration coordinates and lift-off coordinates reach a first axis. One example of such a rotation is represented in FIG. 4, wherein the calibration, lift-off, and inspection coordinates are rotated until the calibration coordinates 415A and lift-off coordinates 415B reach the first axis 302. Another example of such a rotation is represented in FIG. 5, wherein the calibration, lift-off, and inspection coordinates are rotated until the lift-off coordinates 415B are disposed above the first axis 302 and spaced from the first axis by at least the preset threshold 408.

In step 980, an indicator is activated if the rotated inspection coordinates are at least disposed above the first axis. Activation of the indicator represents a situation wherein an operator is alerted to the likely presence of a defect in the structure under inspection, for example, as shown in FIG. 7. If the indicator is activated, the operator may perform further inspections and, if the structure under inspection is an aircraft component, the flight of the aircraft may be delayed or even cancelled. For example, the operator may summon NDI specialists who may utilize additional inspection devices and methods to determine the extent of the damages.

A branch 990 is shown in FIG. 9 to illustrate optional additional iterations of steps 950 through 980. That is, in at least one embodiment of the method 900, the ultrasonic transducer is disposed sequentially in multiple locations near the impact site. For example, the transducer might be moved among multiple locations that together surround the impact site. At any such location, the operator observes the indicator and determines whether further inspections are performed according to the judgment or training of the operator. The additional optional iterations represented by branch 990 may be particularly advantageous in inspecting an aircraft component constructed of multiple layers of composite materials. Damages initiating at the surfaces of such constructions typically propagate in expanding cone-patterns into the structures. Thus, damages may be detected by conducting inspections at multiple surface portions surrounding an impact site.

A particular advantage of the inspection system 100 (FIG. 6) resides in the simplicity of its indicator 106. This, in a sense, provides go and no-go test results. An operator without sophisticated training in NDI techniques need not be confounded by complex impedance plane graphical displays. Such an operator can be informed, however, of whether or not significant damages likely reside in an inspected structure. If the indicator 106 is not activated during an inspection session, an inspected structure can be dispatched for use. On the other hand, if the indicator 106 is activated as shown in FIG. 7, the operator can summon specialists trained in inspections, repairs, and repair assessments.

Though several advantages of embodiments of the present invention are described herein, it should be understood that other advantages and other embodiments of the present invention are within the scope of these descriptions. Indeed, many modifications and other embodiments of the invention set forth herein may come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of inspecting a structure, the method comprising:

coupling an ultrasonic transducer with a first structure portion free of defects and determining impedance-plane calibration coordinates corresponding to quadrature-phase separated components of a sinusoidal signal;

lifting the ultrasonic transducer from the first structure portion and determining impedance-plane lift-off coordinates corresponding to quadrature-phase separated components of a sinusoidal signal;

coupling the ultrasonic transducer with a structure portion to be inspected and determining impedance-plane inspection coordinates corresponding to quadrature-phase separated components of a sinusoidal signal;

rotating the calibration coordinates, lift-off coordinates, and inspection coordinates at least until both the calibration coordinates and lift-off coordinates lie upon and are spaced along a first axis such that a first one of the rotated calibration coordinates and a first one of the rotated lift-off coordinates have different values and a second one of the rotated calibration coordinates and a second one of the rotated lift-off coordinates have a common value; and activating an indicator if the rotated inspection coordinates are at least disposed in a predefined relationship to the first axis.

2. The method of claim 1, wherein activating an indicator Comprises activating the indicator if the rotated inspection coordinates are spaced from the first axis by at least a preset threshold.

3. The method of claim 1, further comprising actuating a first switch, while the ultrasonic transducer is coupled with the first structure portion, causing the determination of the calibration coordinates.

4. The method of claim 3, further comprising actuating a second switch, while the ultrasonic transducer is lifted from the first structure portion, causing the determination of the lift-off coordinates.

5. The method of claim 1, wherein rotating the calibration coordinates, lift-off coordinates, and inspection coordinates comprises automatically rotating the calibration coordinates, lift-off coordinates, and inspection coordinates.

6. The method of claim 1, wherein automatically determining whether a defect is present in the airplane structure according to the calibration coordinates, lift-off coordinates, and inspection coordinates comprises automatically rotating the calibration coordinates, lift-off coordinates, and inspection coordinates.

7. A method of inspecting a structure, the method comprising:
coupling an ultrasonic transducer with a first structure portion free of defects and determining impedance-plane calibration coordinates corresponding to quadrature-phase separated components of a sinusoidal signal;
lifting the ultrasonic transducer from the first structure portion and determining impedance-plane lift-off coordinates corresponding to quadrature-phase separated components of a sinusoidal signal;
coupling the ultrasonic transducer with a structure portion to be inspected and determining impedance-plane inspection coordinates corresponding to quadrature-phase separated components of a sinusoidal signal;
rotating the calibration coordinates, lift-off coordinates, and inspection coordinates at least until the calibration coordinates and lift-off coordinates reach a first axis representative of different values of a first one of the coordinates with a second one of the coordinates being zero, wherein rotating the coordinates comprises rotating the calibration coordinates, lift-off coordinates, and inspection coordinates at least until the lift-off coordinates are spaced from the first axis by at least a preset threshold such that the second one of the rotated lift-off coordinates has a value that at least equals the preset threshold; and
activating an indicator if the rotated inspection coordinates are at least disposed in a predefined relationship to the preset threshold.

8. The method of claim 7, further comprising activating the indicator if the ultrasonic transducer is lifted from or otherwise loses coupling with the structure portion to be inspected.

9. The method of claim 7 further comprising inspecting two depth ranges spaced apart within the structure, wherein inspecting two depth ranges comprises determining if a second one of the rotated inspection coordinates at least equals the preset threshold with one depth range corresponding to rotated inspection coordinates closer to the rotated lift-off coordinates than the rotated calibration coordinates and the other depth range corresponding to rotated inspection coordinates closer to the rotated calibration coordinates than the rotated lift-off coordinates.

10. A method of inspecting an airplane structure, the method comprising:
coupling an ultrasonic transducer with a first structure portion free of defects and determining impedance-plane calibration coordinates;
lifting the ultrasonic transducer from the first structure portion and determining impedance-plane lift-off coordinates;
coupling the ultrasonic transducer with an airplane structure to be inspected and determining impedance-plane inspection coordinates; and
automatically determining whether a defect is present in the airplane structure according to the calibration coordinates, lift-off coordinates, and inspection coordinates, wherein automatically determining whether a defect is present comprises:
rotating the calibration coordinates, lift-off coordinates, and inspection coordinates at least until both the calibration coordinates and lift-off coordinates lie upon and are spaced along a first axis such that a first one of the rotated calibration coordinates and a first one of the rotated lift-off coordinates have different values and a second one of the rotated calibration coordinates and a second one of the rotated lift-off coordinates have a common value; and
activating an indicator if the rotated inspection coordinates are at least disposed in a predefined relationship to the first axis.

11. The method of claim 10, further comprising:
actuating a first switch, while the ultrasonic transducer is coupled with the first structure portion, causing the determination of the calibration coordinates; and
actuating a second switch, while the ultrasonic transducer is lifted from the first structure portion, causing the determination of the lift-off coordinates.

12. A system comprising:
an ultrasonic transducer; and
an electronic device comprising an indicator, the electronic device disposed in electrical contact with the ultrasonic transducer and configured for:
determining first impedance plane coordinates for a first structure portion free of defects and determining second impedance plane coordinates when the ultrasonic transducer is lifted from the first structure portion;
energizing the ultrasonic transducer;
receiving sinusoidal signals generated by the ultrasonic transducer;
determining impedance-plane inspection coordinates corresponding to quadrature-phase separated components of the sinusoidal signals generated by the ultrasonic transducer;
rotating the first impedance plane coordinates, the second impedance coordinates, and the inspection coordinates at least until both the first impedance plane coordinates and the second impedance plane coordinates lie upon and are spaced along a first axis such that a first one of the rotated first impedance plane coordinates and a first one of the rotated second impedance plane coordinates have different values and a second one of the rotated first impedance plane coordinates and a second one of the rotated second impedance plane coordinates have a common value;

determining whether at least one impedance plane inspection coordinate exceeds a preset threshold; and automatically activating the indicator if the at least one impedance plane inspection coordinate exceeds the preset threshold.

13. The system of claim 12, wherein the electronic device is configured to automatically rotate the first and second impedance plane coordinates.

14. The system of claim 13, wherein the electronic device is configured to automatically rotate the first and second impedance plane coordinates until the second impedance plane coordinates exceed the preset threshold.

15. The system of claim 12, wherein the electronic device comprises an adjustment device by which the preset threshold is adjustable.

16. The system of claim 12, wherein the electronic device comprises a housing in which the adjustment device is protected from casual access.

17. The system of claim 12, wherein the electronic device comprises an adjustment device by which the rotation is adjustable.

18. The system of claim 12, wherein the indicator comprises a light source.

19. A system comprising:

an ultrasonic transducer; and an electronic device comprising an indicator, the electronic device disposed in electrical contact with the ultrasonic transducer and configured for:

determining first impedance plane coordinates for a first structure portion free of defects and determining second impedance plane coordinates when the ultrasonic transducer is lifted from the first structure portion;

energizing the ultrasonic transducer;

receiving sinusoidal signals generated by the ultrasonic transducer;

determining impedance-plane inspection coordinates corresponding to quadrature-phase separated components of the sinusoidal signals generated by the ultrasonic transducer;

rotating the first impedance plane coordinates, second impedance plane coordinates, and inspection coordinates at least until the first impedance plane coordinates and second impedance plane coordinates reach a first axis representative of different values of a first one of the coordinates with a second one of the coordinates being zero, wherein rotating the coordinates comprises rotating the first impedance plane coordinates, second impedance plane coordinates, and inspection coordinates at least until the second impedance plane coordinates are spaced from the first axis by at least a preset threshold such that the second one of the rotated second impedance plane coordinates has a value that at least equals the preset threshold;

determining whether at least one impedance plane inspection coordinate exceeds the preset threshold; and automatically activating the indicator if the at least one impedance plane inspection coordinate exceeds the preset threshold.

20. A system of claim 19 wherein the electronic device being configured to determine whether at least one impedance plane inspection coordinate exceeds the preset threshold comprises the electronic device being configured to inspect two depth ranges spaced apart within a structure by determining if a second one of the rotated inspection coordinates at least equals the preset threshold with one depth range corresponding to rotated inspection coordinates closer to the rotated second impedance plane coordinates than the rotated first impedance plane coordinates and the other depth range corresponding to rotated inspection coordinates closer to the rotated first impedance plane coordinates than the rotated second impedance plane coordinates.

* * * * *